(12) United States Patent
Nagare et al.

(10) Patent No.: US 9,034,375 B2
(45) Date of Patent: May 19, 2015

(54) WATER-IN-OIL EMULSION COMPOSITION

(75) Inventors: Yuko Nagare, Yokohama (JP); Kazuhiro Yamaguchi, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 13/639,520

(22) PCT Filed: Apr. 11, 2011

(86) PCT No.: PCT/JP2011/058979
§ 371 (c)(1),
(2), (4) Date: Oct. 5, 2012

(87) PCT Pub. No.: WO2011/129290
PCT Pub. Date: Oct. 20, 2011

(65) Prior Publication Data
US 2013/0022563 A1    Jan. 24, 2013

(30) Foreign Application Priority Data

Apr. 13, 2010  (JP) ................................. 2010-092261
Apr. 8, 2011   (JP) ................................. 2011-086012

(51) Int. Cl.
| A61K 9/66 | (2006.01) |
| A61K 8/49 | (2006.01) |
| A61K 8/06 | (2006.01) |
| A61K 8/27 | (2006.01) |
| A61K 8/894 | (2006.01) |
| A61Q 17/04 | (2006.01) |

(52) U.S. Cl.
CPC .............. *A61K 8/4966* (2013.01); *A61K 8/064* (2013.01); *A61K 8/27* (2013.01); *A61K 8/894* (2013.01); *A61Q 17/04* (2013.01)

(58) Field of Classification Search
CPC ....... A61K 8/4966; A61K 8/064; A61K 8/27; A61K 8/894
See application file for complete search history.

(56) References Cited

U.S. PATENT DOCUMENTS

2009/0017081 A1*  1/2009  Takakura et al. ............. 424/401
2010/0284950 A1   11/2010  Müller

FOREIGN PATENT DOCUMENTS

| EP | 1051963 | 11/2000 |
| JP | H9-118726 | 5/1987 |
| JP | 5-238924 | 9/1993 |
| JP | H7-291837 | 11/1995 |
| JP | 9-118926 | 5/1997 |
| JP | 2002-155189 | 5/2002 |
| JP | 2004-91374 | 3/2004 |
| JP | 2004-519499 | 7/2004 |
| JP | 2005-350367 | 12/2005 |
| JP | 2009-091307 | 4/2009 |
| JP | 2010-47538 | 3/2010 |
| JP | 5058352 | 8/2012 |
| WO | WO 2009/007264 | 1/2009 |

OTHER PUBLICATIONS

Jennifer Allen, Cornelius Technical Centre, Trends in tanning, Mar. 2010, Retrieved from URL:<http://www.corneliuspolska.pl/publikacje_i_artykuly/trends_in_tanning/$File/ALLEN_SunCare2010.pdf>, pp. 30-32.*
JPO Notice of Reasons for Rejection of Sep. 16, 2011, Certified English translation (3pgs); Japanese (3 pgs), for JP App. No. 2011-86012.
Applicant's Written amendment to JPO, filed on Nov. 14, 2011, cert. English translation (1 pg) for JP App. No. 2011-86012; Applicant's Written argument to JPO, filed on Nov. 14, 2011, cert. English translation (3 pgs) for JP App. No. 2011-86012; Applicant's Written amendment and Arguments to JPO of Nov. 14 Japanese (3 pgs) for JP App. No. 2011-86012.
JPO decision to grant on Jul. 27, 2012 for JP App. No. 2011-86012, Certified Englished Translation (3 pgs); JPO decision to grant on Jul. 27, 2012 for JP App. No. 2011-86012, Japanese (3 pgs).
JP-B-5058352-Granted Claims, Certified English Translation (2 pgs).
Certificate of Accuracy for English Translation, Mar. 26, 2013.
International Serach Report for PCT/JP2011/058977, dated Sep. 20, 2011, English 3 pgs and JP 3 pgs.
JP 2012/7027202, Korean Office Action mailed Aug. 26, 2014, English—3 pages; Japanese—3 pages; Korean—4 pages.
EP 11768811.9, European Office Action and Search Report, dated Jan. 17, 2014, English—17 pages.

(Continued)

*Primary Examiner* — Lezah Roberts
*Assistant Examiner* — Nannette Holloman
(74) *Attorney, Agent, or Firm* — Andrew F. Young, Esq.; Lackenbach Siegel, LLP

(57) ABSTRACT

A water-in-oil emulsion composition which contains a low water-solubility but oil-soluble ultraviolet absorber, and which exhibits excellent ultraviolet light protection and stability. The composition contains (a) an aqueous dispersion of an oil-soluble ultraviolet absorber; (b) a polyoxyalkylene-modified polysiloxane having a molecular mass of at least 2000; and (c) at most 5 mass % of an ultraviolet scattering agent; and component (a) being contained in the internal phase. Component (a) is preferably an aqueous dispersion of a complex particle of an oil-soluble ultraviolet absorber and an organic polymer.

13 Claims, 1 Drawing Sheet

(56) References Cited

OTHER PUBLICATIONS

Technical Disclosure, PriorArtDatabase, "Polymer dispersions of encapsulated organic UV Filters in Personal Care"; Authors: Disclosed Anonymously, IP.com Electronic Publication: Jan. 17, 2009; Copyright © IP.com, Inc., IP.com No. IPCOM000177948D, 50 pages—English.

Technical Disclosure, PriorArtDatabase, "Suncare compositions with new cosmetic raw materials"; Authors: Disclosed Anonymously, IP.com Electronic Publication: Mar. 2, 2010; Copyright © IP.com, Inc., IP.com No. IPCOM000193556D, 118 pages—English.

* cited by examiner

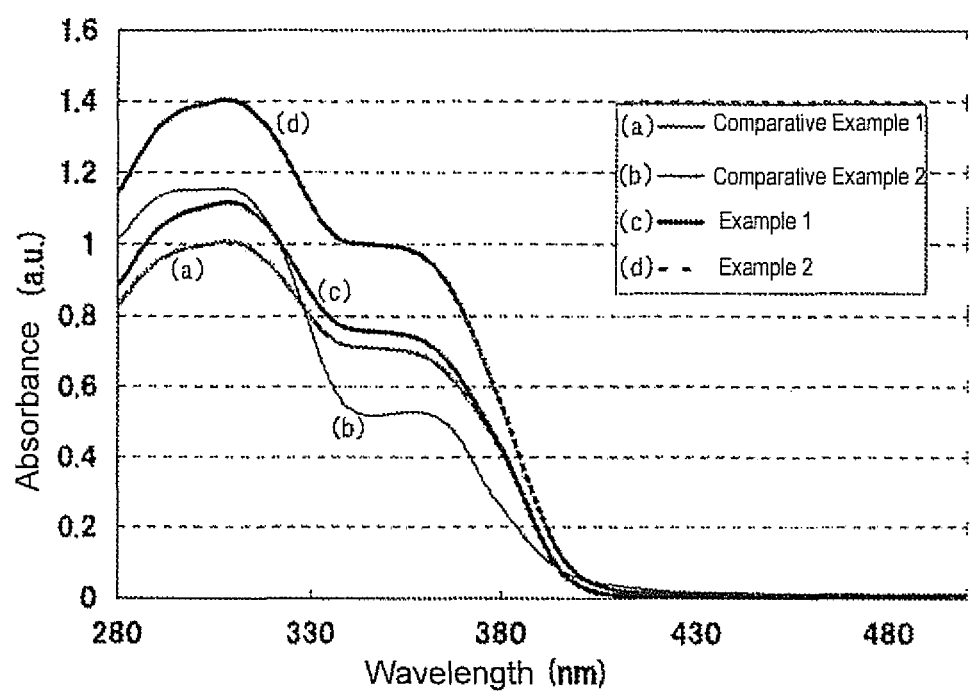

WATER-IN-OIL EMULSION COMPOSITION

CROSS REFERENCE TO RELATED APPLICATIONS

This application claims priority to International Ser. No. PCT/JP2011/058,979 filed Apr. 11, 2011, the entire contents of which are incorporated herein fully by reference, and which in turn claims the priority of JP Patent Application Ser. No. JP 2010-092261, filed on Apr. 13, 2010 and JP 2011-086012, filed on Apr. 8, 2011, the entirety of both applications are hereby incorporated by references.

TECHNICAL FIELD

The present invention relates to a water-in-oil emulsion composition, and more particularly, to a water-in-oil emulsion composition containing an oil-soluble ultraviolet absorber in an internal phase (water phase), and having a high stability and ultraviolet protection ability.

BACKGROUND ART

Sunscreen cosmetics are intended to block ultraviolet rays in the sunlight to protect the skin from adverse effects of ultraviolet rays. Conventionally, to attain a high ultraviolet protection ability, an ultraviolet scattering agent such as particulate zinc oxide needs to be blended. However, if a large amount of ultraviolet scattering agent is blended, some problems arise such that the resultant product causes squeaky feeling in sense of use and that the skin to which the resultant product is applied becomes unnaturally white.

On the other hand, oil-soluble ultraviolet absorbers such as 2,4-bis-{[4-(2-ethylhexyloxy)-2-hydroxy]phenyl}-6-(4-methoxyphenyl)-(1,3,5)-triazine (hereinafter, referred to as "bis-ethylhexyloxyphenol methoxyphenyl triazine" in the present specification) have a high ultraviolet protective effect; however, most of the oil-soluble ultraviolet absorbers are less soluble, which caused a stability problem in some cases such that an ultraviolet absorber precipitated in an oil phase at a low temperature.

For example, Patent Document 1 describes that a less soluble ultraviolet absorber is encapsulated in spherical polymer particles formed of styrene or the like and made into a spherical powder, with the result that solubility in oil is improved to attain a high content in an oil phase; however, cases where the ultraviolet absorber are blended in a water phase are not known.

PRIOR ART PUBLICATIONS

Patent Document

Patent Document 1: JP-A-2009-91307

SUMMARY OF THE INVENTION

Problem to be Solved by the Invention

Therefore, an object of the present invention is to provide a water-in-oil emulsion composition which contains an oil-soluble ultraviolet absorber having a low solubility, and has good sense of use and also an excellent ultraviolet absorption ability and stability.

Means for Solving the Problem

To attain the object, the present invention provides a water-in-oil emulsion composition containing (a) an aqueous dispersion of an oil-soluble ultraviolet absorber, (b) a polyoxyalkylene modified polysiloxane having a molecular weight of 2000 or more and (c) 5% by mass or less of an ultraviolet scattering agent, in which the component (a) is contained in an internal phase.

In the present invention, the component (a) is preferably an aqueous dispersion of composite particles of an oil-soluble ultraviolet absorber and an organic polymer.

Effects of the Invention

The water-in-oil type emulsion composition of the present invention containing an ultraviolet absorber less soluble in oil in an internal phase (water phase) provides an improved stability of the system. Furthermore, the water-in-oil emulsion composition can exert an advantageous effect of improving ultraviolet protection ability, compared to that containing the same ultraviolet absorber in an oil phase (external phase). Moreover, since water-in-oil emulsion composition of the present invention contains an ultraviolet scattering agent only in a predetermined amount or less, good sense of use is attained without causing squeaky feeling and in addition a high ultraviolet protection ability and excellent stability can be obtained.

BRIEF DESCRIPTION OF DRAWING

FIG. 1 is a chart showing ultraviolet absorption spectra of the compositions of Examples 1 and 2 and Comparative Examples 1 and 2.

MODES FOR CARRYING OUT THE INVENTION

The water-in-oil emulsion composition of the present invention contains an aqueous dispersion of an oil-soluble ultraviolet absorber (component a) in an internal phase (water phase).

The oil-soluble ultraviolet absorber is not particularly limited; however, it is preferably selected from ultraviolet absorbers insoluble in water and less soluble in oil. However, substances substantially insoluble in oil such as methylene bis-benzotriazole tetramethylbutyl phenol, are not included. If an oil-in-water emulsion composition is prepared using a water dispersion of an ultraviolet absorber insoluble in oil and applied to the skin, the resultant skin sometimes looks unnaturally white.

Examples of the less-soluble ultraviolet absorber include those described in Patent Document 1 described above. Specific examples thereof include benzophenone derivatives and triazine derivatives, especially, triazine derivatives are preferable. Among these triazine derivatives, bis-ethylhexyloxyphenol methoxyphenyl triazine is preferable. The bis-ethylhexyloxyphenol methoxyphenyl triazine is commercially available from BASF under the trade name of Tinosorb S, and the commercially available product can be used.

Furthermore, the aqueous dispersion of an oil-soluble ultraviolet absorber in the present invention is particularly preferably an aqueous dispersion of composite particles of an oil-soluble ultraviolet absorber and an organic polymer. When a water phase containing the aqueous dispersion is present together with an oil, the incorporation of the oil-soluble ultraviolet absorber into the composite particles suppress the dissolution of the oil-soluble ultraviolet absorber in the water phase into the oil phase.

The aqueous dispersion of composite particles of an oil-soluble ultraviolet absorber and an organic polymer can be prepared, for example, in accordance with a method described in WO2009/007264. In short, emulsion polymerization is performed in the state of dispersing a mixture of an ultraviolet absorber and an organic monomer in water to obtain an aqueous dispersion having composite particles of the ultraviolet absorber and an organic polymer dispersed therein.

As the organic monomer, a monomer having an ethylenic unsaturated bond, such as acrylic acid, methacrylic acid, an alkyl acrylate, an alkyl methacrylate, a styrene monomer and a nylon monomer, is preferably used.

As an aqueous dispersion of such composite particles, a commercially available product from BASF under the trade name of Tinosorb S aqua can be used. Tinosorb S aqua contains composite particles of bis-ethylhexyloxyphenol methoxyphenyl triazine (Tinosorb S) and polymethylmethacrylate (PMMA) dispersed in water. The contents of bis-ethylhexyloxyphenol methoxyphenyl triazine and PMMA are 20% by mass and 19% by mass, respectively.

The content of the oil-soluble ultraviolet absorber in the composition of the present invention is 5% by mass or less, preferably 3% by mass or less, and more preferably 0.01 to 3% by mass, on a dry mass basis. If the content is less than 0.01% by mass, a sufficient ultraviolet absorption ability cannot be obtained; whereas, if the content is beyond 5% by mass, it tends to cause a problem in sense of use, such as greasiness.

Note that, provided that an aqueous dispersion (component a) contains 20% by mass of the ultraviolet absorber, the content in terms of the aqueous dispersion is 25% by mass or less, preferably 15% by mass or less, and more preferably 0.05 to 15% by mass.

The water-in-oil emulsion composition of the present invention contains a polyoxyalkylene modified polysiloxane having a molecular weight of 2000 or more as an emulsifier.

Examples of the polyoxyalkylene modified polysiloxane to be used in the present invention include a POE-methyl polysiloxane copolymer, a silicone chain branched type POE-methyl polysiloxane copolymer, a crosslinked type POE-methyl polysiloxane copolymer, an alkyl-POE co-modified methyl polysiloxane copolymer and a silicone chain branched type alkyl-POE co-modified methyl polysiloxane copolymer. As commercially available products, ABIL EM90 of Evonik Goldschmidt GmbH, KF-6017, KF-6028, KF-6038 of Shin-Etsu Chemical Co., Ltd. and BY22-008 M, BY11-030 and 5200 Formulation Aid of Dow Corning Toray Co., Ltd. are preferably used.

A preferable polyoxyalkylene modified polysiloxane has a molecular weight of 2000 or more, and suitably 6000 or more. The upper limit of the molecular weight of the polyoxyalkylene modified polysiloxane in the present invention is not particularly limited; however, it is usually about 8000 or less.

An emulsion composition of the present invention may contain one or two or more polyoxyalkylene modified polysiloxanes having a molecular weight of 2000 or more, and suitably 6000 or more (hereinafter referred to as a "polyoxyalkylene modified polysiloxane having a specified molecular weight").

In the emulsion composition of the present invention, the addition amount of polyoxyalkylene modified polysiloxane having a specified molecular weight is preferably 7.5% by mass or less, more preferably 5% by mass or less, and further preferably 0.01 to 3% by mass usually based on the composition. If the addition amount is less than 0.01% by mass, it is sometimes difficult to sufficiently perform water-in-oil emulsification; whereas, if the addition amount is beyond 7.5% by mass, it is confirmed that the resultant emulsion composition tends to deteriorate in the sense of use, causing greasiness.

In the emulsion composition of the present invention, if an ultraviolet scattering agent is further blended in a predetermined amount or less, an ultraviolet blocking effect can be further improved.

As the ultraviolet scattering agent, particulate zinc oxide and/or particulate titanium dioxide is preferably used.

As the particulate zinc oxide used herein, particulate zinc oxide having an average particle size of 0.1 μm or less (the lower limit of the average particle size is not particularly limited; however, it is usually about 30 nm) generally used in external use compositions such as cosmetics, is preferable and can be produced by a conventional method such as the French method or the American method and a commercially available product may also be used. Examples of the commercially available particulate zinc oxide include FINEX-25, FINEX-50 and FINEX-75 (manufactured by Sakai Chemical Industry Co., Ltd.), ZnO350 (manufactured by Sumitomo Osaka Cement Co., Ltd.), ZINCOX SUPER-10, ZINCOX SUPER-20R, ZINCOX SUPER-30 and ZINCOX CP-1 (manufactured by HakusuiTech Co., Ltd.); Z-COTE (manufactured by SunSmart); and MZ-500 and MZ-700 (manufactured by Tayca Corp.).

The particulate titanium dioxide used herein is particulate titanium dioxide having an average particle size of 0.1 μm or less (the lower limit of the average particle size is not particularly limited; however, it is usually about 30 nm) generally used in external use compositions such as cosmetics, and can be produced by a conventional method such as the sulfuric acid method or the chlorine method and a commercially available product may also be used. Examples of the commercially available particulate titanium dioxide include SIV series, TTO-55 series and TTO-S series (manufactured by Ishihara Sangyo Kaisha, Ltd.); and MT-100TV, MT-500V and MT-01 (manufactured by Tayca Corp).

Furthermore, the ultraviolet scattering agent (e.g., particulate zinc oxide and particulate titanium dioxide) to be used in the present invention is preferably a hydrophobized powder prepared by hydrophobizing the surface of particles.

Examples of a hydrophobizing agent for producing the hydrophobized powder include, but not particularly limited to, a silicone processing agent, a fatty acid, a fatty acid soap and a fatty acid ester. Examples of the silicone processing agent include various types of silicone oils such as methyl hydrogen polysiloxane, dimethylpolysiloxane and methylphenyl polysiloxane; various types of alkyl silanes such as methyl trimethoxysilane, ethyl trimethoxysilane, hexyl trimethoxysilane and octyl trimethoxysilane; and various types of fluoroalkyl silanes such as trifluoromethylethyl trimethoxysilane and heptadecafluorodecyl trimethoxysilane. Furthermore, examples of the fatty acids include palmitic acid, isostearic acid, stearic acid, lauric acid, myristic acid, behenic acid, oleic acid, rosin acid and 12-hydroxystearic acid. Furthermore, examples of the fatty acid soap include aluminum stearate, calcium stearate and aluminum 12-hydroxystearate. Furthermore, examples of the fatty acid ester include dextrin fatty acid ester, cholesterol fatty acid ester, sucrose fatty acid ester and starch fatty acid ester. By using one or more of these hydrophobizing agents, the hydrophobizing treatment of a particulate powder can be performed in accordance with a conventional method.

Note that, needless to say, particulate metal oxide powders having an ultraviolet blocking effect other than the particulate zinc oxide or particulate titanium dioxide, such as particulate iron oxide, particulate cerium oxide and particulate tungsten oxide, preferably those processed with hydrophobizing treatment, can be blended as an ultraviolet scattering agent in the emulsion composition of the present invention.

The content of the ultraviolet scattering agent in the emulsion composition of the present invention is not particularly limited; however, preferably 5% by mass or less, more preferably 3% by mass or less, and further preferably 2% by mass or less based on the composition. Particularly, the water-in-oil emulsion composition of the present invention is more improved in ultraviolet protective effect by blending an oil-soluble (less soluble) ultraviolet absorber in the internal phase (water phase) in the form of an aqueous dispersion. The effect is also sufficient without addition of the ultraviolet scattering agent. Accordingly, the emulsion composition of the present invention may or may not contain an ultraviolet scattering agent. Even if the US scattering agent is contained, the content thereof can be suppressed. Thus, a problem in sense of use such as squeaky feeling is not caused.

Furthermore, the emulsion composition of the present invention can be more improved in emulsion stability by blending a water-swelling clay mineral in combination with a quaternary ammonium salt type cation surfactant.

When a water-swelling clay mineral is blended in combination with a quaternary ammonium salt type cation surfactant, these are brought into contact with each other to form a specific organic modified clay mineral, which conceivably contributes to improving stability of emulsion composition (hereinafter, unless otherwise specified, the "organic modified clay mineral" refers to the organic modified clay mineral defined above).

A method for preparing an organic modified clay mineral is described in detail in, e.g., Japanese Patent Laid-open No. 2-14098. The outline thereof will be described below.

A water-swelling clay mineral is a type of colloid-containing aluminum silicate having a trilaminar structure and generally represented by the following formula (1).

$$(X, Y)_{2-3}(Si,Al)_4O_{10}(OH)_2Z_{1/3} \cdot nH_2O \quad (1)$$

wherein X is Al, Fe(III), Mn(III) or Cr(III); Y is Mg, Fe(II), Ni, Zn or, Li; and Z is K, Na, or Ca.

Specific examples of such a water-swelling clay mineral include bentonite, smectite, montmorillonite, beidellite, nontronite, saponite and hectorite. These may be either one of a natural product and a synthetic product. Examples of commercially available products include, Kunipia (manufactured by Kunimine Industries Co., Ltd.), Smecton (manufactured by Kunimine Industries Co., Ltd.), VEEGUM (manufactured by Vanderbilt Company, Inc.), Laponite (manufactured by Laporte) and fluoro-tetrasilisic mica (manufactured by TOPY Industries Ltd.).

In the meantime, as the quaternary ammonium salt type cation surfactant, the surfactants represented by the following formula (2) are preferably used.

[Formula 1]

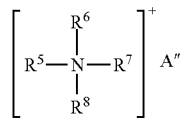  (2)

wherein $R^5$ represents an alkyl group having 10 to 22 carbon atoms or a benzyl group; $R^6$ represents a methyl group or an alkyl group having 10 to 22 carbon atoms; $R^7$ and $R^8$ represent an alkyl group or a hydroxyalkyl group having 1 to 3 carbon atoms; and A represents a halogen atom or a methyl sulfate residue.

Specific examples of the quaternary ammonium salt type cation surfactant include dodecyl trimethyl ammonium chloride, myristyl trimethyl ammonium chloride, cetyl trimethyl ammonium chloride, stearyl trimethyl ammonium chloride, arachyl trimethyl ammonium chloride, behenyl trimethyl ammonium chloride, cetyl dimethyl ammonium chloride, stearyl dimethyl ammonium chloride, arachyl dimethyl ammonium chloride, behenyl dimethyl ammonium chloride, cetyl diethyl ammonium chloride, stearyl diethyl ammonium chloride, arachyl diethyl ammonium chloride, behenyl diethyl ammonium chloride, benzyl dimethyl myristyl ammonium chloride, benzyl dimethyl cetyl ammonium chloride, benzyl dimethyl stearyl ammonium chloride, benzyl dimethyl behenyl ammonium chloride, benzyl dimethyl ethyl cetyl ammonium chloride, benzyl dimethyl ethyl stearyl ammonium chloride, distearyl dimethyl ammonium chloride, dibehenyl dihydroxyethyl ammonium chloride and bromides corresponding to these. Furthermore, dipalmityl propyl ethyl ammonium methyl sulfate may be included.

These quaternary ammonium salt type cation surfactants are each preferably used within the range of 60 to 140 mm equivalent based on the water-swelling clay mineral (100 g) as mentioned above. If the content of the quaternary ammonium salt type cation surfactant is less than 60 mm equivalent, emulsification cannot be favorably performed; whereas, if the content is beyond 140 mm equivalent, it is confirmed that stability of the composition over time tends to deteriorate.

As the organic modified clay mineral thus obtained, a commercially available product can also be used. As such a commercially available product, BENTONE 38 (manufactured by Elementis Specialties) or the like can be included.

In the embodiment of the present invention, the content of the water-swelling clay mineral and the quaternary ammonium salt type cation surfactant in the emulsion composition, as the total mass of both components based on the composition, is preferably 0.1 to 10% by mass and particularly preferably 1 to 5% by mass.

Furthermore, in the emulsion composition containing an organic modified clay mineral, if a nonionic surfactant and/or a fatty acid in a liquid state at a normal temperature and/or a higher alcohol in a liquid state at a normal temperature are further added, emulsion stability thereof can be further improved.

The nonionic surfactant to be used in this embodiment is a nonionic surfactant having an HLB value of preferably 2 to 16, and particularly preferably 3 to 12.

Specific examples thereof include ether surfactants such as polyoxyethylene (2 to 30 moles) added [hereinafter, sometimes expressed as POE (2 to 30)] oleyl ether, POE (2 to 35) stearyl ether, POE (1 to 20) alkyl phenyl ether, POE (6 to 18) behenyl ether, POE (5 to 25) 2-decylpentadecyl ether, POE (3 to 30) 2-decyltetradecyl ether and POE (8 to 16) 2-octyldecyl ether;

ester surfactants such as POE (4 to 60) hydrogenated castor oil, POE (3 to 14) fatty acid monoester , POE (6 to 30) fatty acid diester and POE (5 to 20) sorbitan fatty acid ester;

ether ester surfactants such as POE (2 to 30) glyceryl monoisostearate, POE (10 to 60) glyceryl triisostearate, POE (7 to 50) hydrogenated castor oil monoisostearate and POE (12 to 60) hydrogenated castor oil triisostearate; and polyhydric alcohol fatty acid ester surfactants such as decaglyceryl tetraoleate, hexaglyceryl triisostearate, diglyceryl diisostearate and glyceryl monooleate.

Furthermore, the fatty acid in a liquid state at a normal temperature (specifically, about 10 to 35° C., hereinafter the same is applied) is not particularly limited as long as it is a fatty acid which can be contained in an external use composition, etc. Examples thereof include oleic acid, isostearic acid, linoleic acid, linolenic acid, eicosapentaenoic acid and docosahexaenoic acid. One or two or more fatty acids selected from these may be blended.

Furthermore, the higher alcohol in the liquid state at a normal temperature is not particularly limited as long as it is higher alcohol which can be contained in an external use composition, etc. Examples thereof include oleyl alcohol, isostearyl alcohol, octyl dodecanol, decyl tetradecanol and jojoba alcohol. One or two or more higher alcohols selected from these may be blended.

The nonionic surfactant, and/or fatty acid in the liquid state at a normal temperature and/or higher alcohol in the liquid state at a normal temperature, is/are preferably contained in a mass ratio within the range of 0.01 to 5, and further preferably within the range of 0.05 to 4 based on the water swelling clay mineral as mentioned above. If the mass ratio is less than 0.01, emulsification is not favorably performed in many cases. Conversely, if the mass ratio is beyond 5, it is confirmed that stability of the composition over time tends to deteriorate.

The emulsion composition of the present invention may further contain other ultraviolet absorbers in addition to the aforementioned aqueous dispersion of an oil-soluble ultraviolet absorber (component a) to be added to a water phase.

The other ultraviolet absorbers are preferably oil-soluble and dissolved in an oil phase (external phase) and preferably absorb ultraviolet synergistically with the ultraviolet absorber (component a) present in a water phase.

Examples of such an ultraviolet absorber include, but not particularly limited to, a methoxycinnamic acid derivative, a diphenyl acrylic acid derivative, a salicylic acid derivative, a paraaminobenzoic acid derivative, a triazine derivative, a benzophenone derivative, a benzalmalonate derivative, an anthranil derivative, an imidazoline derivative, a 4,4-diarylbutadiene derivative and phenyl benzimidazole derivative. Specific examples thereof include 2-ethylhexyl paramethoxycinnamate; homosalate, octyl salicylate, oxybenzone, 4-t-butyl-4'-methoxydibenzoylmethane, octyl triazone, bis-ethylhexylphenol methoxyphenyltriazine, methylene bis-benzotriazolyl tetramethylbutyl phenol, 2-hydroxy-4-methoxybenzophenone, dihydroxydimethoxybenzophenone, dihydroxybenzophenone, tetrahydroxybenzophenone, hexyl diethylamino hydroxybenzoyl benzoate, 2-cyano-3,3-diphenylacrylic acid 2'-ethylhexyl ester, polysilicone-15 and drometrizole polysiloxane.

In the emulsion composition of the present invention, in addition to the aforementioned components, other components which can be usually used in external use composition such as cosmetics can be contained as long as it does not substantially suppress a desired effect of the present invention.

The oil which can be contained in the emulsion composition of the present invention is not particularly limited and for example, the following substances may be included.

Examples of a silicone oil include linear polysiloxanes (e.g., dimethylpolysiloxane, methylphenylpolysiloxane, diphenylpolysiloxane); cyclic polysiloxanes (e.g., octamethylcyclotetrasiloxane, decamethylcyclopentasiloxane, dodecamethylcyclohexasiloxane), silicone resins forming a three-dimensional network structure, silicone rubbers, and various types of modified polysiloxanes (e.g., amino modified polysiloxane, polyether modified polysiloxane, alkyl modified polysiloxane, fluorine modified polysiloxane). In particular, when volatile cyclic polysiloxane is added, a flesh and comfortable sense of use can be provided.

Examples of a liquid fat and oil include avocado oil, camellia oil, turtle oil, macadamia nut oil, corn oil, mink oil, olive oil, rapeseed oil, egg yolk oil, sesame oil, persic oil, wheat germ oil, sasanqua oil, castor oil, linseed oil, safflower oil, cottonseed oil, perilla oil, bean oil, peanut oil, tea seed oil, Japanese nutmeg oil, rice bran oil, China wood oil, Japanese tung oil, jojoba oil, germ oil and triglycerin.

Examples of a solid fat and oil include cacao butter, coconut oil, horse fat, hardened coconut oil, palm oil, beef tallow, mutton tallow, hardened beef tallow, palm kernel oil, lard, beef bone fat, Japan wax kernel oil, hardened oil, cow leg fat, Japan wax and hydrogenated castor oil.

Examples of a wax include beeswax, candelilla wax, cotton wax, carnauba wax, bayberry wax, Ibota wax, whale wax, montan wax, rice bran wax, lanolin, kapok wax, acetated lanolin, liquid lanolin, sugarcane wax, isopropyl lanolate, hexyl laurate, reduced lanolin, jojoba wax, hard lanolin, shellac wax, POE lanolin alcohol ether, POE lanolin alcohol acetate, POE cholesterol ether, lanolin fatty acid polyethylene glycol and POE hydrogenated lanolin alcohol ether.

Examples of a hydrocarbon oil include liquid paraffin, ozocerite, squalane, pristane, paraffin, ceresin, squalene, Vaseline and microcrystalline wax.

Examples of a higher fatty acid include lauric acid, myristic acid, palmitic acid, stearic acid, behenic acid, oleic acid, undecylenic acid, tall oil acid, isostearic acid, linoleic acid, linolenic acid, eicosapentaenoic acid (EPA) and docosahexaenoic acid (DHA).

Examples of a higher alcohol include linear alcohols (e.g., lauryl alcohol, cetyl alcohol, stearyl alcohol, behenyl alcohol, myristyl alcohol, oleyl alcohol, cetostearyl alcohol); and branched alcohols (e.g., monostearyl glyceryl ether (batyl alcohol), 2-decyl tetradecynol, lanolin alcohol, cholesterol, phytosterol, hexyldodecanol, isostearyl alcohol, octyldodecanol).

Examples of a synthetic ester oil include isopropyl myristate, cetyl octanoate, octyldodecyl myristate, isopropyl palmitate, butyl stearate, hexyl laurate, myristyl myristate, decyl oleate, hexyldecyl dimethyl octanoate, cetyl lactate, myristyl lactate, lanolin acetate, isocetyl stearate, isocetyl isostearate, cholesteryl 12-hydroxystearate, ethylene glycol di-2-ethylhexanoate, dipentaerythritol fatty acid ester, N-alkyl glycol monoisostearate, neopentyl glycol dicaprate, diisostearyl malate, glycerin di-2-heptyl undecanoate, trimethylolpropane tri-2-ethylhexanoate, trimethylolpropane triisostearate, pentaerythritol tetra-2-ethylhexanoate, glycerin tri-2-ethylhexanoate, glycerin trioctanoate, glycerin triisopalmitate, trimethylolpropane triisostearate, cetyl 2-ethylhexanoate, 2-ethylhexyl palmitate, glycerin trimyristate, glyceride tri-2-heptylundecanoate, castor oil fatty acid methyl ester, oleyl oleate, acetoglyceride, 2-heptylundecyl palmitate, diisobutyl adipate, N-lauroyl-L-glutamic acid-2-octyldodecyl ester, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate and triethyl citrate.

Furthermore, examples of the powder component which can be contained in the emulsion composition of the present invention include inorganic powders (e.g., talc, kaolin, mica, sericite, muscovite, phlogopite, synthetic mica, lepidolite, biotite, vermiculite, magnesium carbonate, calcium carbonate, aluminum silicate, barium silicate, calcium silicate, magnesium silicate, strontium silicate, a tungstic acid metal salt, magnesium, silica, zeolite, barium sulfate, a baked calcium sulfate (calcined gypsum), calcium phosphate, fluorine apatite, hydroxy apatite, ceramic powder, boron nitride) metallic soap (e.g., zinc myristate, calcium palmitate, aluminum stearate); organic powders (e.g., a polyamide resin powder (nylon powder), a polyethylene powder, a polymethyl methacrylate powder, a polystyrene powder and styrene-acrylic acid copolymer resin powder, polyurethane powder, benzoguanamine resin powder, a polytetrafluoroethylene powder, a cellulose powder); a silicone powder, a silicone elastic powder; inorganic white pigments [e.g., titanium dioxide, zinc oxide (usually not fine particles)]; inorganic red pigments (e.g., iron oxide (colcothar), iron titanate); inorganic brown pigments (e.g., γ-iron oxide); inorganic yellow pigments (e.g., yellow iron oxide, yellow soil); inorganic black pigments (e.g., black iron oxide, low valence titanium dioxide); inorganic purple pigments (e.g., mango violet, cobalt violet); inorganic green pigments (e.g., chromium oxide, chromium hydroxide, cobalt titanate); inorganic blue pigments (e.g., ultramarine, Berlin blue); pearl pigments (e.g., titanium dioxide coated mica, titanium dioxide coated bismuth oxychloride, titanium dioxide coated talc, colored titanium dioxide coated mica, bismuth oxychloride, fish scale guanine); metal powder pigments (e.g., aluminium powder, copper powder); organic pigments such as zirconium, barium or aluminium lake (e.g., organic pigments such as Red 201, Red 202, Red 204, Red 205, Red 220, Red 226, Red 228, Red 405, Orange 203, Orange 204, Yellow 205, Yellow 401, and Blue 404; Red 3, Red 104, Red 106, Red 227, Red 230, Red 401, Red 505, Orange 205, Yellow 4, Yellow 5, Yellow 202, Yellow 203, Green3 and Blue 1); and natural pigments (e.g., chlorophyll, β-carotene).

Other substances including a surfactant expect the aforementioned nonionic surfactants, a moisturizing agent, a thickening agent, a sequestering agent, a lower alcohol, a polyhydric alcohol, sugar, an amino acid, an organic amine, a polymer emulsion, a pH adjuster, a skin nutrient, a vitamin, an antioxidant, an auxiliary antioxidant, a fragrance and water, if necessary, are appropriately blended to be able to produce the present emulsion composition in accordance with a desired dosage by a conventional method.

EXAMPLES

The present invention will be described in more detail by way of specific examples below; however, the present invention is not limited to the following Examples. Furthermore, the contents shown in the following Examples and the like are expressed by % by mass, if not otherwise specified.

Examples and Comparative Examples

Water-in-oil emulsion compositions having compositions shown in the following Tables 1 and 2 were prepared. To describe more specifically, an oil-phase portion except cation modified bentonite and a powder was heated to 70° C. to be homogeneously dissolved. In the oil-phase portion, the cation modified bentonite was dispersed by a homomixer, and thereafter, various types of hydrophobized powders and other powders were added and dispersed by a homomixer. Separately a water phase portion was prepared and gradually added to the oil-phase portion prepared as described above and emulsified by use of a homomixer. The resultant emulsion composition was degassed and charged in a predetermined container to prepare each sample.

Then, each of the samples prepared was placed in a 50 mL screw tube, and a small amount of bis-ethylhexyloxyphenol methoxyphenyl triazine was added thereto in a solid state. Each of the mixtures, after being stored at 0° C. for one week, was observed by a microscope to evaluate stability of the oil phases. These results are collectively shown in Tables 1 and 2, in which the case where crystals in the amount equal to or larger than the addition amount were observed is expressed as Poor and the case where the crystals in the amount equal to or larger than the addition amount were not observed is expressed as Good.

Furthermore, 40 ml of each of compositions of each Examples was placed in a vial of 50 ml in volume, closed airtight and placed in a 50° C. constant-temperature vessel. The state after a month, particularly the state of emulsion particles, was observed by an optical microscope and evaluated in accordance with the following evaluation criteria (emulsion stability). At this time, since a sample was dispersed in two layers, the emulsion particles were observed after the sample had been shaken well.

<Evaluation Criteria>

Excellent: Unification of emulsion particles is not observed.

Good: Unification of emulsion particles is slightly observed.

Fair: Unification of emulsion particles is observed and the size of emulsion particles is 1.5 times or more than the initial size.

Poor: Unification of emulsion particles is observed and the size of emulsion particles is twice or more than the initial size.

Furthermore, each of the obtained compositions was evaluated with regard to sense of use by 10 female panelists in accordance with the following criteria. Each of the samples was actually applied to their skin in order to evaluate the sense of use (absence of squeaky feeling). The results are collectively shown in Table 1.

Excellent: 8 or more persons evaluated that it caused no squeaky feeling.

Good: 5 to 7 persons evaluated that it caused no squeaky feeling.

Fair: 3 to 4 persons evaluated that it caused no squeaky feeling.

Poor: 2 or less persons evaluated that it caused no squeaky feeling.

A sample (18.87 μL) was taken from each of the compositions of Examples 1 and 2 and Comparative Example 1 and 2 and uniformly applied to a surface of a film made of PMMA (5 cm×5 cm) in a ratio of 0.75 mg/cm². After the film was allowed to stand still for 15 minutes, absorbance of each of the samples was measured by using a spectrophotometer (U-4100: manufactured by Hitachi, Ltd.). The results of the measurements are shown in FIG. 1.

TABLE 1

| | | Comparative Example 1 | Comparative Example 2 | Example 1 | Example 2 |
|---|---|---|---|---|---|
| Water phase | Ion exchange water | Balance | Balance | Balance | Balance |
| | Ethyl alcohol | 5 | 5 | 5 | 5 |
| | 1,3 Butylene glycol | 5 | 5 | 5 | 5 |
| | Glycerin | 3 | 3 | 3 | 3 |
| | Trisodium edetate | 0.05 | 0.05 | 0.05 | 0.05 |

TABLE 1-continued

|  |  | Comparative Example 1 | Comparative Example 2 | Example 1 | Example 2 |
|---|---|---|---|---|---|
|  | Phenoxy ethanol | 0.5 | 0.5 | 0.5 | 0.5 |
|  | Water dispersion of bis-ethylhexyloxyphenol methoxyphenyl triazine*1) | — | — | 15 | 15 |
| Oil phase | Decamethylcyclopentasiloxane | 32 | 32 | 32 | 32 |
|  | Dimethylpolysiloxane | 5 | 5 | 5 | 5 |
|  | Olefin oligomer | 2 | 2 | 2 | 2 |
|  | Diisopropyl sebacate | 5 | 5 | 5 | 5 |
|  | Trimethylsiloxy silicate | 5 | 5 | 5 | 5 |
|  | Polyoxyalkylene modified polysiloxane*2) | 3 | 3 | 3 | 3 |
|  | 4-t-Butyl-4'-methoxydibenzoylmethane | 1 | 1 | 1 | 1 |
|  | 2-Ethylhexyl paramethoxycinnamate | 5 | 5 | 5 | 5 |
|  | bis-Ethylhexyloxyphenol methoxyphenyl triazine | 3 | — | — | — |
|  | Cation modified bentonite*3) | 0.5 | 0.5 | 0.5 | 0.5 |
|  | Nylon powder | 5 | 5 | 5 | 5 |
|  | Silicone coated particulate zinc oxide*4) | — | 8 | — | 1 |
| Total |  | 100 | 100 | 100 | 100 |
| Sense of use |  | Excellent | Poor | Excellent | Excellent |
| Crystal precipitation |  | Poor | Good | Good | Good |
| Emulsion stability |  | Excellent | Excellent | Excellent | Excellent |

*1)Tinosorb S Aqua (manufactured by BASF)
*2)KF-6028 (manufactured by Shin-Etsu Chemical Co., Ltd.)
*3)BENTONE 38 (manufactured by Elementis Specialties)
*4)Treated with silicone 3%, FINEX-50 (manufactured by Sakai Chemical Industry Co., Ltd.)

TABLE 2

|  |  | Example 3 | Example 4 | Example 5 | Example 6 |
|---|---|---|---|---|---|
| Water phase | Ion exchange water | Balance | Balance | Balance | Balance |
|  | Ethyl alcohol | 5 | 5 | 5 | 5 |
|  | 1,3 Butylene glycol | 5 | 5 | 5 | 5 |
|  | Glycerin | 3 | 3 | 3 | 3 |
|  | Trisodium edetate | 0.05 | 0.05 | 0.05 | 0.05 |
|  | Phenoxy ethanol | 0.5 | 0.5 | 0.5 | 0.5 |
|  | Water dispersion of bis-ethylhexyloxyphenol methoxyphenyl triazine*1) | 15 | 15 | 15 | 15 |
| Oil phase | Decamethylcyclopentasiloxane | 32 | 32 | 32 | 32 |
|  | Dimethylpolysiloxane | 5 | 5 | 5 | 5 |
|  | Olefin oligomer | 2 | 2 | 2 | 2 |
|  | Diisopropyl sebacate | 5 | 5 | 5 | 5 |
|  | Trimethylsiloxy silicate | 5 | 5 | 5 | 5 |
|  | Polyoxyalkylene modified polysiloxane*2) | 3 | 3 | 3 | 3 |
|  | 4-t-Butyl-4'-methoxydibenzoylmethane | 1 | 1 | 1 | 1 |
|  | 2-Ethylhexyl paramethoxycinnamate | 5 | 5 | 5 | 5 |
|  | bis-Ethylhexyloxyphenol methoxyphenyl triazine | — | — | — | — |
|  | Cation modified bentonite*3) | 0.5 | 0.5 | — | 3 |
|  | Nylon powder | 5 | 5 | 5 | 5 |
|  | Silicone coated particulate zinc oxide*4) | 3 | 5 | 3 | 5 |
| Total |  | 100 | 100 | 100 | 100 |
| Sense of use |  | Excellent | Good | Excellent | Good |
| Crystal precipitation |  | Good | Good | Good | Good |
| Emulsion stability |  | Excellent | Excellent | Good | Excellent |

*1)Tinosorb S Aqua (manufactured by BASF)
*2)KF6028 (manufactured by Shin-Etsu Chemical Co., Ltd.)
*3)BENTONE 38 (manufactured by Elementis Specialties)
*4)Treated with silicone 3%, FINEX-50 (manufactured by Sakai Chemical Industry Co., Ltd.)

In Comparative Example 1 where bis-ethylhexyloxyphenol methoxyphenyl triazine was blended in an oil phase, crystal precipitation was observed at a low temperature (0° C.), which caused a problem in stability. In contrast, in Examples 1 to 6 where the same ultraviolet absorber was blended in a water phase in the form of an aqueous dispersion, no crystal precipitation was observed. Thus, the emulsion was stable.

In Comparative Example 2 where an ultraviolet scattering agent (8%) was blended, sense of use was inferior; however, in Examples 1 to 6 where the ultraviolet scattering agent was 5% or less, sense of use was superior.

Furthermore, Examples 1 to 4 and 6 where an organic modified clay mineral was blended were improved in emulsion stability compared to Example 5 where the organic modified clay mineral was not blended.

From the results shown in FIG. 1, it became apparent that the composition (Example 1) where bis-ethylhexyloxyphenol methoxyphenyl triazine was blended in the form of an aqueous dispersion in a water phase, exhibits an excellent ultraviolet absorption ability compared to Comparative Example 1 where bis-ethylhexyloxyphenol methoxyphenyl triazine was blended in an oil phase. Furthermore, the composition (Example 1) of the present invention where bis-ethylhexyloxyphenol methoxyphenyl triazine was blended in the form of an aqueous dispersion in a water phase, exhibited a sufficient ultraviolet protective effect although a ultraviolet scattering agent was not added.

Cosmetics composed of water-in-oil type emulsion compositions in accordance with the following formulation were prepared.

Formulation Example 1

Sunscreen Milky Lotion

| | |
|---|---|
| Decamethylcyclopentasiloxane | 10 |
| Isododecane | 10 |
| Polyoxyalkylene modified polysiloxane copolymer | 1 |
| Olefin oligomer | 5 |
| Dimethylpolysiloxane | 5 |
| Caprylyl methicone | 2 |
| Isopropyl myristate | 2 |
| Octyl palmitate | 2 |
| 2-Ethylhexyl paramethoxycinnamate | 10 |
| Polysilicone-15 | 2 |
| Hexyl diethylaminohydroxybenzoylbenzoate | 3 |
| An aqueous dispersion of bis-ethylhexyloxyphenol methoxyphenyl triazine | 10 |
| Hydrophobized zinc oxide | 5 |
| Cation modified saponite | 0.5 |
| 1,3-Butylene glycol | 5 |
| Glycerin | 3 |
| Ion exchange water | balance |
| Fragrance | q.s. |
| Chelating agent | q.s. |

Formulation Example 2

Sunscreen Milky Lotion

| | |
|---|---|
| Dimethicone | 15 |
| Decamethylcyclopentasiloxane | 5 |
| Phenyl trimethicone | 3 |
| Polyoxyalkylene modified polysiloxane copolymer | 1 |
| Squalane | 2 |
| Cetyl 2-ethylhexanoate | 2 |
| Isononyl isononanoate | 2 |
| Pentaerythritol tetra-2-ethylhexanoate | 2 |
| Dimethylpolysiloxane | 5 |
| 2-Ethylhexyl paramethoxycinnamate | 5 |
| 2-Cyano-3,3-diphenylacrylic acid 2'-ethylhexyl ester | 5 |
| 4-t-Butyl-4'-methoxydibenzoylmethane | 3 |
| Phenylbenzimidazole sulfonic acid | 2 |
| Aqueous dispersion of bis-ethylhexyloxyphenol methoxyphenyl triazine | 15 |
| Cation modified hectorite | 0.2 |
| Hydrophobized titanium dioxide | 3 |
| Hydrophobized zinc oxide | 2 |
| PMMA powder | 6 |
| Paraben | 0.5 |
| Glycerin | 3 |
| Dipropylene glycol | 2 |
| Ion-exchange water | balance |
| Fragrance | q.s. |
| Chelating agent | q.s. |

Formulation Example 3

Sunscreen Cream

| | |
|---|---|
| Decamethylcyclopentasiloxane | 20 |
| Isohexadecane | 1 |
| Polyoxyalkylene modified polysiloxane copolymer | 3 |
| Cetyl isooctanoate | 10 |
| Dimethylpolysiloxane | 5 |
| Glyceryl tri(2-ethylhexanoate) | 2 |
| Diisopropyl sebacate | 2 |
| 2-Ethylhexyl paramethoxycinnamate | 5 |
| 2-Cyano-3,3-diphenylacrylic acid 2'-ethylhexyl ester | 3 |
| Aqueous dispersion of bis-ethylhexyloxyphenol methoxyphenyl triazine | 5 |
| Methylene bis-benzotriazolyl tetramethylbutyl phenol | 1 |
| 2-hydroxy-4-methoxybenzophenone | 1 |
| Ion exchange water | balance |
| 1,3-butyleneglycol | 2 |
| Dipropylene glycol | 1 |
| Cation modified bentonite | 2.5 |
| Hydrophobized titanium dioxide | 1 |
| Hydrophobized zinc oxide | 2 |
| Silica powder | 6 |
| Phenoxy ethanol | 0.5 |
| Fragrance | q.s. |
| Chelating agent | q.s. |

Formulation Example 4

Sunscreen Milky Solution

| | |
|---|---|
| Decamethylcyclopentasiloxane | 25 |
| Dimethicone (1.5CS) | 15 |
| Polyoxyalkylene modified polysiloxane copolymer | 2 |
| Diisopropyl adipate | 10 |
| Caprylyl methicone | 5 |
| Alkyl ($C_{12-15}$) benzoate | 4 |
| 2-Cyano-3,3-diphenylacrylic acid 2'-ethylhexyl ester | 8 |
| Aqueous dispersion of bis-ethylhexyloxyphenol methoxyphenyl triazine | 12 |
| Methylene bis-benzotriazolyl tetramethylbutyl phenol | 5 |
| (Dimethicone/vinyl dimethicone) crosspolymer | 5 |
| Ion exchange water | balance |
| 1,3-Butyleneglycol | 2 |
| PEG-400 | 1 |
| Magnesium sulfate | 0.5 |

| Ascorbic acid-2glucoside | 2 |
| Hydrophobized titanium dioxide | 1 |
| Hydrophobized zinc oxide | 2 |
| Nylon-12 powder | 6 |
| Phenoxy ethanol | 0.5 |
| Fragrance | q.s. |
| Chelating agent | q.s. |

The invention claimed is:

1. A water-in-oil emulsion composition comprising:
   (a) an aqueous dispersion of an oil-soluble ultraviolet absorber;
   (b) a polyoxyalkylene modified polysiloxane having a molecular weight of 2000 or more; and
   (c) 5% by mass or less of an ultraviolet scattering agent;
   wherein the oil-soluble ultraviolet absorber is bis-ethylhexyloxyphenol methoxyphenyl triazine, and wherein the component (a) is contained in an internal phase.

2. The composition according to claim 1, wherein the component (a) is an aqueous dispersion of composite particles of an oil-soluble ultraviolet absorber and an organic polymer.

3. The composition according to claim 1, wherein the content of the oil-soluble ultraviolet absorber is 0.01 to 3% by mass.

4. The composition according to claim 1, wherein the (b) polyoxyalkylene modified polysiloxane has a molecular weight of 6000 or more.

5. The composition according to claim 1, further comprising a water-swelling clay mineral and a quaternary ammonium salt cation surfactant.

6. The composition according to claim 1, wherein the (c) ultraviolet scattering agent is zinc oxide.

7. The composition according to claim 2, wherein the content of the oil-soluble ultraviolet absorber is 0.01 to 3% by mass.

8. The composition according to claim 2, wherein the (b) polyoxyalkylene modified polysiloxane has a molecular weight of 6000 or more.

9. The composition according to claim 3, wherein the (b) polyoxyalkylene modified polysiloxane has a molecular weight of 6000 or more.

10. The composition according to claim 2, further comprising a water-swelling clay mineral and a quaternary ammonium salt cation surfactant.

11. The composition according to claim 4, further comprising a water-swelling clay mineral and a quaternary ammonium salt cation surfactant.

12. The composition according to claim 2, wherein the (c) ultraviolet scattering agent is zinc oxide.

13. The composition according to claim 4, wherein the (c) ultraviolet scattering agent is zinc oxide.

* * * * *